(12) United States Patent
Hudson et al.

(10) Patent No.: US 9,704,096 B2
(45) Date of Patent: Jul. 11, 2017

(54) METHOD AND SYSTEM FOR MAKING CUSTOMIZED FORMULATIONS FOR INDIVIDUALS

(71) Applicant: Panacea Biomatx, Inc., Research Triangle Park, NC (US)

(72) Inventors: Edison Thurman Hudson, Chapel Hill, NC (US); Lloyd Staton Noel, Durham, NC (US)

(73) Assignee: Panacea Biomatx, Inc., Research Triangle Park, NC (US)

( * ) Notice: Subject to any disclaimer, the term of this patent is extended or adjusted under 35 U.S.C. 154(b) by 516 days.

(21) Appl. No.: 14/207,364

(22) Filed: Mar. 12, 2014

(65) Prior Publication Data

US 2014/0279792 A1    Sep. 18, 2014

Related U.S. Application Data

(60) Provisional application No. 61/777,181, filed on Mar. 12, 2013.

(51) Int. Cl.
| | |
|---|---|
| *A61J 1/06* | (2006.01) |
| *G06N 5/02* | (2006.01) |
| *G06F 19/00* | (2011.01) |
| *A61J 3/00* | (2006.01) |

(52) U.S. Cl.
CPC ............ *G06N 5/02* (2013.01); *A61J 1/062* (2013.01); *A61J 3/002* (2013.01); *G06F 19/3475* (2013.01)

(58) Field of Classification Search
CPC .... A61K 2300/00; A61K 45/06; A61Q 19/00; G06F 19/328
See application file for complete search history.

(56) References Cited

U.S. PATENT DOCUMENTS

| | | | |
|---|---|---|---|
| 3,640,741 A | 2/1972 | Etes | |
| 6,632,457 B1 | 10/2003 | Sawhney | |
| 6,702,894 B2 | 3/2004 | Lee et al. | |
| 6,782,307 B2 | 8/2004 | Wilmott et al. | |
| 6,881,449 B2 | 4/2005 | Augello et al. | |
| 6,975,924 B2 | 12/2005 | Kircher et al. | |
| 7,115,297 B2 | 10/2006 | Stillman | |
| 7,295,889 B2 | 11/2007 | Lahteenmaki | |

(Continued)

FOREIGN PATENT DOCUMENTS

| | | |
|---|---|---|
| GB | 2389357 A | 12/2003 |
| KR | 20110061399 A | 6/2011 |

OTHER PUBLICATIONS

EPO, Extended European Search Report for European Patent Application No. 14779095.0, mailed on Jul. 18, 2016.

(Continued)

*Primary Examiner* — Reginald R Reyes
(74) *Attorney, Agent, or Firm* — NK Patent Law, PLLC

(57) ABSTRACT

The one or more embodiments disclosed herein provide a method for automatically assembling multiple compounds into a single edible custom composition, in which each compound is individually customized to proportions formulated from a profile of an individual or group. The single custom mixture can contain a plurality of compounds including foods or flavors, nutritional additives, herbals, biologics, or pharmacologically active substances. Using the method and a related algorithm, the formulation of a custom mixture is suggested.

31 Claims, 18 Drawing Sheets

(56) References Cited

U.S. PATENT DOCUMENTS

| | | | |
|---|---|---|---|
| 7,457,685 B2 | 11/2008 | D'Silva | |
| 7,574,844 B2 * | 8/2009 | Kamineni | A61J 1/20 |
| | | | 53/239 |
| 7,762,181 B2 | 7/2010 | Boland et al. | |
| 7,899,713 B2 | 3/2011 | Rothschild | |
| 7,974,856 B2 | 7/2011 | Jung et al. | |
| 8,000,982 B2 | 8/2011 | Kane et al. | |
| 8,249,946 B2 | 8/2012 | Froseth et al. | |
| 8,323,718 B2 | 12/2012 | Kopesky et al. | |
| 8,335,592 B2 | 12/2012 | Deo et al. | |
| 8,417,377 B2 | 4/2013 | Rothschild | |
| 8,442,674 B2 | 5/2013 | Tilton et al. | |
| 8,449,920 B2 | 5/2013 | Niichel | |
| 8,523,067 B2 | 9/2013 | Stone et al. | |
| 8,545,892 B2 | 10/2013 | Niichel | |
| 8,573,263 B2 | 11/2013 | Bartholomew et al. | |
| 2002/0082745 A1 | 6/2002 | Wilmott et al. | |
| 2003/0010791 A1 | 1/2003 | Gentiluomo et al. | |
| 2004/0172169 A1 | 9/2004 | Wright, IV et al. | |
| 2005/0210834 A1 * | 9/2005 | Kamineni | A61J 1/20 |
| | | | 53/415 |
| 2006/0099310 A1 | 5/2006 | Koekkoek | |
| 2009/0181376 A1 * | 7/2009 | Becker | G01N 33/6848 |
| | | | 435/6.12 |
| 2010/0015184 A1 * | 1/2010 | Tuel | A61K 9/00 |
| | | | 424/400 |
| 2010/0266723 A1 | 10/2010 | Bralley et al. | |
| 2011/0014351 A1 | 1/2011 | Reider et al. | |
| 2011/0054928 A1 | 3/2011 | Sullivan | |
| 2011/0251243 A1 | 10/2011 | Tucker et al. | |
| 2012/0041778 A1 | 2/2012 | Kraft | |
| 2012/0277180 A1 | 11/2012 | Marini et al. | |
| 2013/0045319 A1 | 2/2013 | Forns | |
| 2013/0053446 A1 | 2/2013 | Muzzio et al. | |
| 2013/0216616 A1 | 8/2013 | Alfano | |
| 2013/0295597 A1 * | 11/2013 | DeWitte | G01N 30/06 |
| | | | 435/23 |

OTHER PUBLICATIONS

Sahay, Drop on Demand Technology as a Mini Manufacturing Platform for Drug Delivery and Personalized Medicine, Jan. 2012.
ISRP for application No. PCT/US2014/025047 mailed Sep. 4, 2014.
Form PCT/IB/326 (IPRP Transmittal Notification) mailed Sep. 24, 2015 for PCT application No. PCT/US2014/025047.
Form PCT/IB/373 (IPRP that includes the PCT/ISA/237—Written Opinion) issued Sep. 15, 2015 for PCT application No. PCT/US2014/025047.
Vitaganic, www.vitaganic.com, 2005, 2 pages.
Customvite, www.Customvite.com, 2013, 2 pages.
Customvite, About Page, www.customevite.com, 2013. 1 page.
Helkio, Takala, "Ink-Jet Printing of Pharmaceuticals", 8th International DAAAM Baltic Conference, Apr. 19-21, 2012, 6 pages.
Carney, Micahel, "Fitkit Launches Personalized, Doctor-Curated Nutritional Supplements, Delivered to Your Door." www.pandodail.com, Sep. 4, 2012, 9 pages.
EPO, Examination Report for European Patent Application No. 14779095.0 mailed Mar. 9, 2017.

* cited by examiner

| Summary | |
|---|---|
| Melatonin is a neurohormone produced in the brain. Levels of melatonin in the blood are highest prior to bedtime. Melatonin products have been used for many medical conditions. It is most often used for people who have insomnia (trouble sleeping). | |
| Uses | |
| These uses have been tested in humans or animals. Safety and effectiveness have not always been proven. Some of these conditions are potentially serious, and should be evaluated by a qualified healthcare provider. | Grade |
| Jet lag | A |
| Delayed sleep phase syndrome (DSPS) | B |
| Insomnia (in the elderly) | B |
| Sleep disorders (children with behavioral, developmental, and intellectual disorders) | B |
| Sleep enhancement in healthy people | B |
| Age-related macular degeneration | C |
| Aging (changes in body temperature) | C |
| Anti-inflammatory | C |
| Anxiety (before surgery) | C |
| Benzodiazepine tapering | C |

Administrator Toolbar | Jump to page [Page 1 ▾]

0%

This is my profile

Your Sex
☐ Male
☐ Female

Age
[_____]

Weight (Approximate in lbs)
[_____]

Drugs you take everyday
Prescription drugs only

Aspirin [____▾]
Statins [____▾]
Blood thinner [____▾]
Others [____▾]

[Submit]

METHOD AND SYSTEM FOR MAKING CUSTOMIZED FORMULATIONS FOR INDIVIDUALS

CROSS-REFERENCE TO RELATED APPLICATIONS

This application claims priority to U.S. Provisional Patent Application No. 61/777,181, filed on Mar. 12, 2013, the contents of which are hereby incorporated by reference herein.

TECHNICAL FIELD

This disclosure includes a method and system for assembling a subset of multiple compounds into a single, edible composition. This disclosure includes a method and system for assembling multiple compounds into a single, edible composition, in which each compound is individually customized to proportions formulated from a profile of an individual or group.

BACKGROUND

There is a need for customized formulations of dietary supplements and therapeutics based on the genetic, physical, physiological, and medical needs of an individual. Conventionally, typical formulations of supplements and therapeutics are prepared as a pill or liquid in batches comprised of a fixed set of ingredients to be used by the average person with little regard to the needs of that specific individual. Often times these "one size fits all" predetermined formulations contains ingredients and quantities that are conflicting with the individual's needs and requirements.

As individual genomic sequencing, molecular diagnostics, such as, for example, laboratory diagnostics or point of care tests, and advanced individual digital heath testing becomes more economic and prevalent, the fields of pharmacogenomics, nutrigenomics, and metabolomics methods will likely become more commonly adopted manner of proactive health care. These diagnostic advances will drive the need for corresponding innovation in the formulation and packaging of a range of compounds and biologics in a small batch production that is economic for individual consumption. There is a substantial population of individuals with various degrees of dysphagia, xerostomia, and other ailments that may have difficulty swallowing large and/or numerous pills and tablets and chewing their food properly. In addition individuals with cognitive impairment or who are taking a large number of pills need easy to use packaging that facilitates their ability to manage their daily intake of dietary supplements and oral therapeutics. These individuals need alternative forms of dietary supplements and therapeutics that allow for ease of use. Further, there is recognized need to encourage greater consumer compliance in daily intake of key nutritional and pharmacological components in order to obtain desired outcomes, and a solution that uses natural human drives, such as taste and pleasure, if combined to suit individual subjective preferences will likely improve voluntary compliance with prescriptive nutrition and medicine.

A need therefore exists for a method or solution that addresses these disadvantages.

SUMMARY

This Summary is provided to introduce a selection of concepts in a simplified form that are further described below in the Detailed Description of Illustrative Embodiments. This Summary is not intended to identify key features or essential features of the claimed subject matter, nor is it intended to be used to limit the scope of the claimed subject matter.

The one or more embodiments disclosed herein provide a method for automatically assembling multiple components into a single edible custom composition, in which each component is individually customized to proportions formulated from a profile of an individual or group. The single custom mixture can contain a plurality of components including foods or flavors, nutritional additives, herbals, biologics, or pharmacologically active substances. Using the method and a related algorithm, the formulation of a custom mixture is suggested.

According to one or more embodiments, the one or more embodiments encompass six subsystems. One of the subsystems may include a database of the physical parameters of an individual along with several or all vital health conditions, including family history, consumption of supplements and pharmaceuticals, and genetic profile of same individual. These may be generated via online questionnaire completed by the individual or advisor, deciphered from medical or family history records, or results of levels of various compounds as determined by laboratory tests or in-situ instrumentation or tests and known or suspected allergens. One of the subsystems includes a database of a multitude of commonly consumed nutritional, biologic, and pharmaceutical compounds with normative dose data, contraindications, depletions, and graded research indicating science evidence correlation score to health conditions. One of the subsystems may include a formulation algorithm implemented in software that automatically cross correlates the health conditions of the individual profile to the compound database selecting those that are deemed to be recommended and which calculates the ratio-metric proportional doses of those selected ingestible compounds that correspond to both the appropriate amount and substance for the individual and their health conditions producing a safe formulation or recipe for a custom mixture of the multiple selected compounds. One or more subsystems may include an online computer review process that allows the user to interact with the recommendation of the formulation algorithm, to vary within safe limits the amounts of each compound, and where desirable or required for safety to obtain a real-time review and approval by a professional dietician, nutritionists, pharmacist, or licensed medical practitioner as required. One or more subsystems may include a semi-solid storage and stable media for the compounds selected such that the individual or multi-compounds are suspended in the media in a uniform and homogeneous distribution throughout the volume of a container for the media. One or more subsystems may include an automation system that converts the formulation recipe for the individual into a machine sequence for a robotic system that can access each of the compound containers of the approved formulation. The compound containers are each equipped with a digitally controlled actuator that delivers the precise volume matching the recommended dose volume of the semi-solid media containing the compound and a digital measuring system to determine amount dispensed to the mixture. The robotic system then accesses each of the compounds selected in the recipe either sequentially or many compounds concurrently and administers a homogenization process to blend all of the components collected into a single dose ready for packaging or immediate use.

BRIEF DESCRIPTION OF THE DRAWINGS

The foregoing summary, as well as the following detailed description of various embodiments, is better understood when read in conjunction with the appended drawings. For the purposes of illustration, there is shown in the drawings exemplary embodiments; however, the presently disclosed subject matter is not limited to the specific methods and instrumentalities disclosed. In the drawings:

FIG. 16 is a screenshot of an online questionnaire for use with the one or more systems and methods disclosed herein;

FIG. 17 is a screenshot of a profile for an individual for use with the one or more systems and methods disclosed herein.

DETAILED DESCRIPTION

Figure 1:
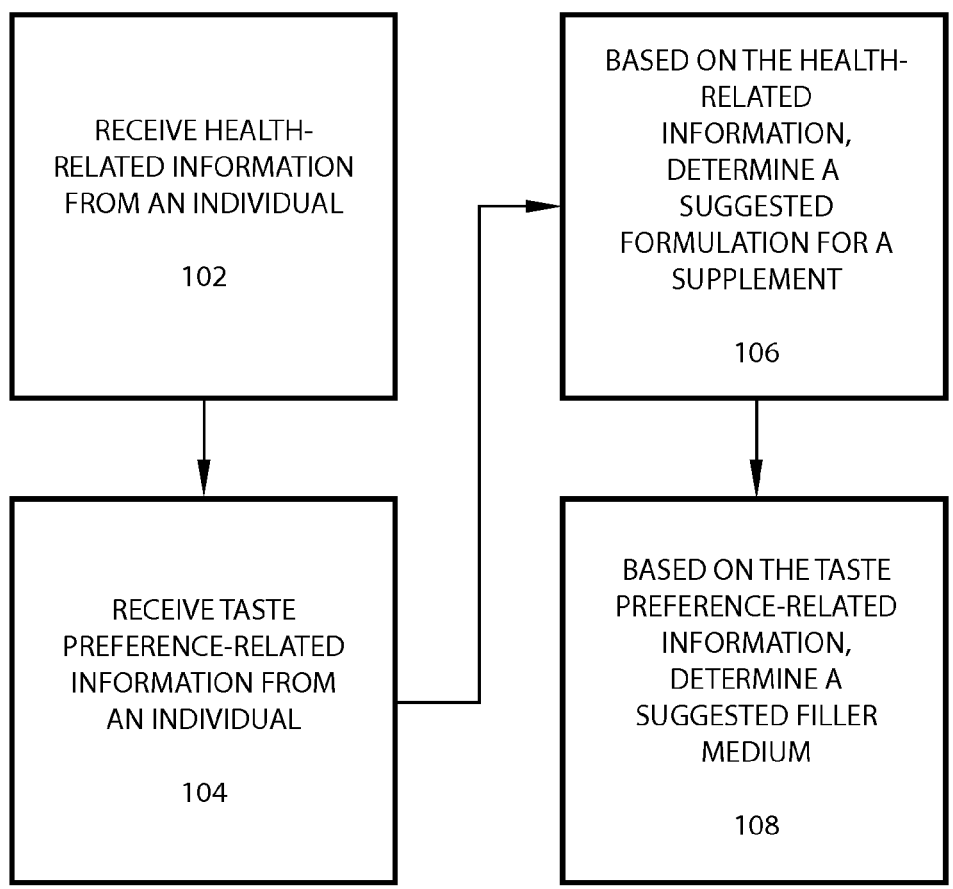
FIG. 1 illustrates one or more methods depicted by the flowchart according to one or more embodiments disclosed herein.

The presently disclosed invention is described with specificity to meet statutory requirements. However, the description itself is not intended to limit the scope of this patent. Rather, the inventors have contemplated that the claimed invention might also be embodied in other ways, to include different steps or elements similar to the ones described in this document, in conjunction with other present or future technologies.

A method to automate a small batch production of dietary nutritionals and pharmaceuticals is disclosed herein. A combination of methods to deliver a plurality of such compounds is integrated into an automation solution that enables economic customization at the level of individual needs and preferences are shown. These automation compatible methods include solutions to a key problem of creating customized formulations that include incompatible solubility amongst the plurality of components one is mixing. Often ingredients are insoluble in water and must be dissolved in other solvents that are not safe for human consumption. In addition mixtures of liquids are unstable, can separate out into separate components, form non-homogenous suspensions, and form undesirable interactions. In one or more embodiments, the small batch production is less than about 5 liters. In one or more embodiments, the small batch production is less than about 1 liter.

One manner of addressing this problem is the creation of semi-solid formulations like hydrogels, organogels, or stable emulsions. Organogels are a type of gel that is formed from a liquid organic phase and a three-dimensional, cross-linked network.

Thixotropic semi-solids suitable for this purpose will have properties that enable the dissolution or suspension of compounds in a form that is stable until agitated or extruded, at which point the semi-solid becomes fluid and can be dispensed. These thixotropic semisolids which are formed via molecular self assembly of cross-linked polymers, which cause the compounds that are agitated in with the hydro or organogels in a liquid state due to elevated temperature or pH, cause the compounds to be embedded with a verifiable solution strength and uniform volumetric concentration of ingredients can act as the components in the building of customized formulations. Soluble and non-soluble components may be fixed in a tangible semi-solid media such a gelatin, agar, and sodium alginate. For instance, semi-solid agar embedded with vitamins, minerals, and other nutrients may be used in the practice of growing bacteria. In addition, agar and other hydrocolloids may be used as a food product and may be useful in the delivery of drugs. By using semi-solid edible material, one can add a customized quantity and list of ingredients to a container blend these components by using a combination of homogenization, heat, change in pH, or addition of cations to re-solubilize the semi-solid gels, and then re-form the gel to a desired final edible product. From a combination of these methods, this invention shows a standardized approach to producing semi-solid matrices that provide a universal compound carrying media that can accommodate dense, uniformly distributed, and stable over time forms that are directly amenable to automation.

One or more methods disclosed herein are illustrated with the flow diagram of FIG. 1, with the method being generally designated 100. The method 100 may include receiving health-related information from an individual 102. This health-related information may be, for example, medical history, height, weight, age, and sex of the individual. One or combinations of each of these sources of information may be provided. The health-related information may also include family history, genetic information, known allergens of the individual, and metabolomic profile data. This may be provided via laboratory baseline tests. In one or more embodiments, the individual may be inputting this data onto a computing device that is in communication with an external server that controls the one or more systems disclosed herein, or this data may be provided by a healthcare service professional.

The method 100 may include receiving taste preference-related information from the individual. The taste preference related data may include favorite tastes, textures, and dosage size as selected by the individual. In this manner, if an individual prefers a grape flavored medium having moderate viscosity and in a small dosage size, this information would be provided. In one or more embodiments, the individual may be inputting this data onto a computing device that is in communication with an external server that controls the one or more systems disclosed herein.

The method 100 may include, based on the health-related information, determining a suggested formulation for a supplement 106. The suggested formulation may be certain levels of any given vitamin or nutritional supplement that the formulation engine (described in further detail herein) determines is appropriate based on the health-related information of the individual.

The method 100 may include, based on the taste preference-related information, determining a suggested filler medium. The suggested filler medium may be a certain filler material of a given weight, viscosity, taste, and volume as further described herein.

Figure 10:
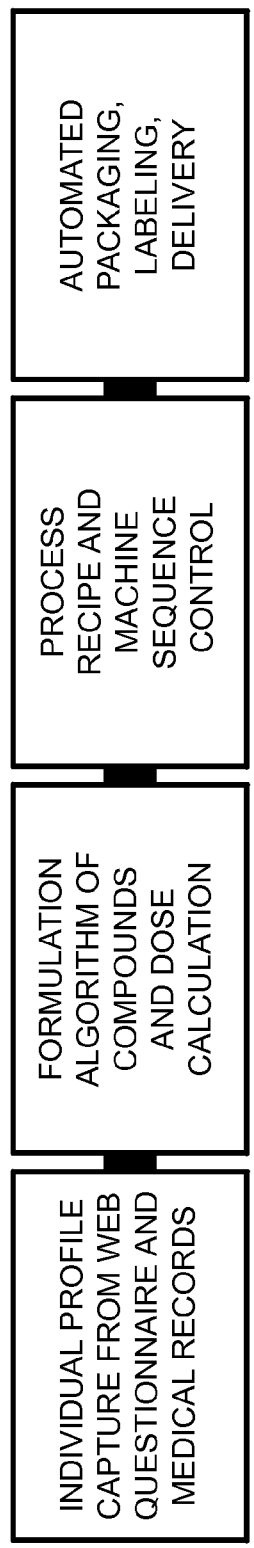
FIG. 10 illustrates a flow diagram of one or more methods according to one or more embodiments disclosed herein.
Figure 11:
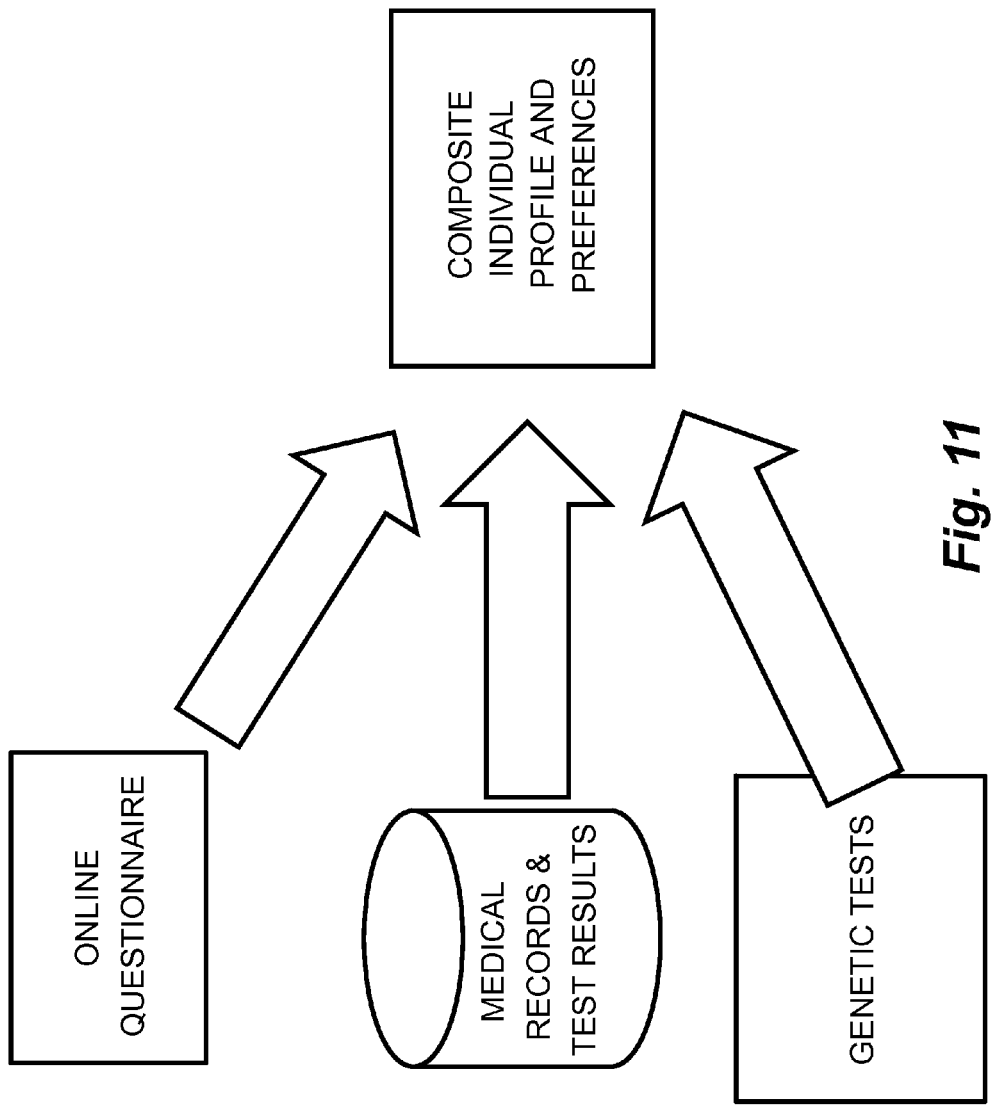
FIG. 11 illustrates a flow diagram of one or more methods according to one or more embodiments disclosed herein.

The systems and methods according to one or more embodiments disclosed herein create a customized formulation from data specific to an individual that facilitates the single dose oral delivery of dietary supplements, vitamins, therapeutic agents, combined in a highly palatable custom mixture with food substances, flavors and textures as may suit the individual tastes. See for example FIGS. 10 and 14. The method includes an automated formulation algorithm that uses correlation and relevance scores to create a list of known and available components for inclusion and proportioned dose of each in the custom mixture, derived from data captured in an individual profile. See for example FIGS. 11 and 12. The one or more methods illustrated in FIG. 11 combine information received from the online questionnaire, medical records and test results, and also genetic tests to compile a composite individual profile and preferences score. This individual profile as determined directly by a questionnaire, either written and encoded, as online responses to a computer interface, or indirectly by other previously captured data sources specific to the individual, and contains at a minimum the current individual's physical attributes and history data such as weight, height, sex, age, and health status, such as pregnant, active, immobile, and the like. See for example FIGS. 11 and 17, with FIG. 17 showing user inputted health related data of a user profile. These basic individual data elements are the parameters of the methods algorithm for ratio metric proportioning of the molecular weight of any component to be included in the custom mixture. The individual profile may also contain a plurality of other relevant data to further refine the recipe generation, including medical history, family medical history, current nutritional, dietary, and pharmacological product consumption. The system algorithm of formulation may also incorporate results of medical test data such as blood pressure, blood sugar, and the like, or from specific medical condition tests, and/or including genetic, proteomic, and metabolomics profiles. The individual's profile is correlated by the system algorithm with a database of a multitude of consumable components containing correlation scores for their relevance to the data captured in the individual profile. This database of components includes the score for efficacy or applicability to the individual's profile, as determined by available scientific and other publically available data, such as the peer reviewed data from the National Institute of Health's Office of Dietary Supplements, The Natural Standard (www. Naturalstandard.Com), Beer's List, and other similar available qualified data set. This database on component attributes supplies the method's algorithm with scores for contraindications, strength of scientific evidence relative to effectiveness for specific conditions, and to the individual's profile or to other components, as well as relevant safety precautions of components taken together. FIG. 16 illustrates a summary chart based on the correlation score.

Figure 12:
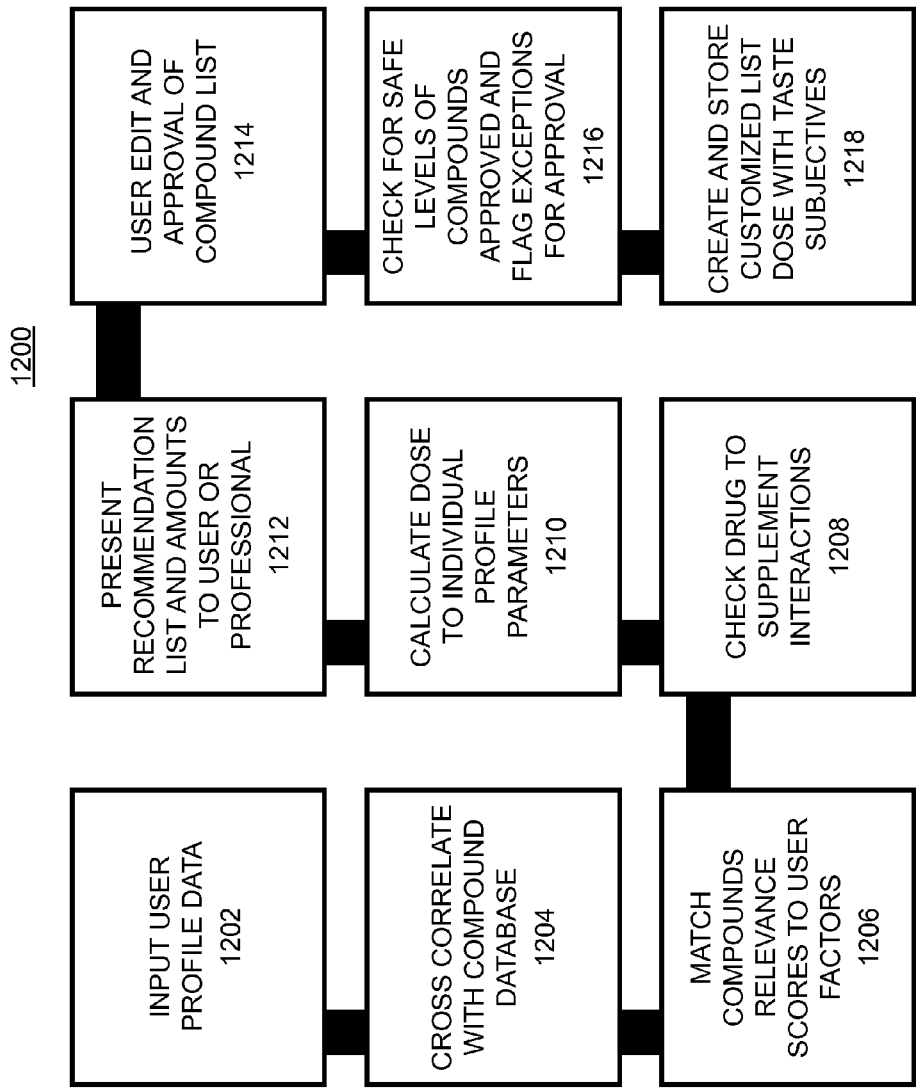
FIG. 12 illustrates a flow diagram of one or more methods according to one or more embodiments disclosed herein.

As illustrated by the flow chart of FIG. 12, one or more methods 1200 disclosed herein may include inputting user profile data 1202. This user profile data may include the health-related and taste preference-related data disclosed herein. The one or more methods 1200 may include cross correlating with a compound database 1204 in order to determine suitable nutritional compounds. The one or more methods 1200 may include matching compound relevance scores to user factors 1206. The one or more methods 1200 may check for drugs taken by the individual/user in order to supplement interactions 1208. The one or more methods 1200 may include calculating a dose to individual profile parameters 1210. The one or more methods 1200 may include presenting a recommendation list and amounts to the individual/user or a professional 1212. The one or more methods 1200 may include allowing the user to edit and approve of the compound list 1214. In this manner, if the user wishes to edit the selected supplements being added to a dosage, they may be able to do so. The one or more methods 1200 may include checking for safe levels of compounds after user edit to check if the compounds are approved and flag any exceptions requiring further review for approval 1216. The one or more methods 1200 may include creating and storing customized list dosages with taste subjectives 1218. Further description of steps of the one or more methods 1200 is disclosed herein.

After the formulation algorithm ("FA") searches the component database as keyed by the individual's profile for relevance, efficacy, and contraindication of all components, the algorithm generates a recommended recipe for the custom mixture. The recipe includes the recommended dose as proportioned to the individual physical parameters and the available dosing information indicated by the manufacturer of the component or by the scientific or public data for that component. The recommended recipe of components to include in the custom mixture as determined by the FA will be presented to the individual for approval, along with a list of the scores of relevancy, efficacy, and online links to the publication or reference for each component being recommended, to be optionally reviewed by the individual consumer. See for example FIG. 12. At this point the individual may edit amounts of the recipe formulation, constrained by safe limitations and contraindications stored in the compounds database, and if desired augment the formulation with other desired compounds or taste, texture, and smell components.

In one or more embodiments, a real time tele-present professional, such as a certified dietician, nutritional counselor, doctor, or other qualified medical professional, such that an online review may be provided of the recommended recipe vis-à-vis the individual's profile. This optional step may be provided whenever the FA flags a potential contraindication or safety issue. In the case of pharmaceutical contraindication, such review would be required by the system and offered online or in due course after review by a pharmacist, doctor, or other certified and licensed medical counselor. See, for example, FIGS. 12 and 13.

Figure 13:
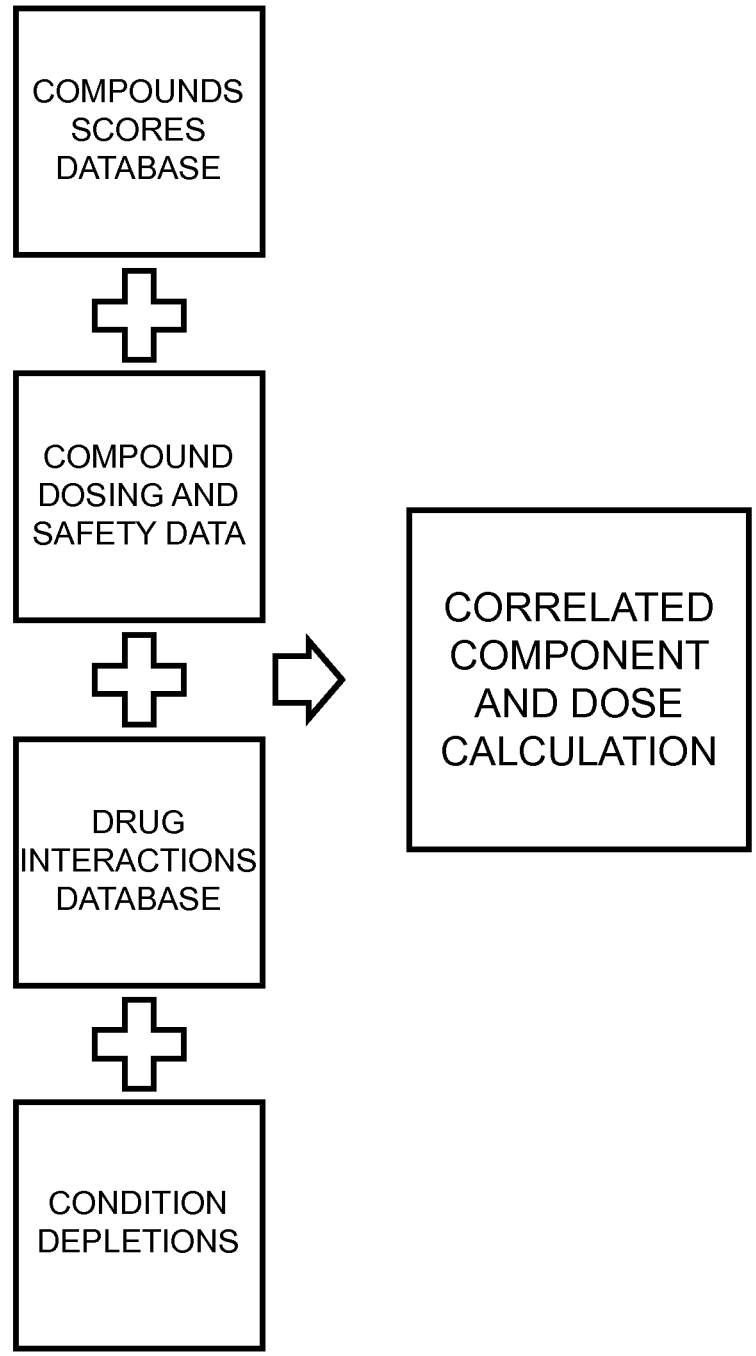
FIG. 13 illustrates a flow diagram of one or more methods according to one or more embodiments disclosed herein.

FIG. 13 illustrates a flow diagram where a correlated component and dose calculation, as further described herein, is calculated based on the compounds scores database, compound dosing and safety data, drug interactions database, and condition depletions.

The individual profile may also include optional flavor, texture, or food components that are subjectively chosen to bring the custom mixture to a more palatable and pleasurable state, as may be within the bounds of the volume and media of the custom mixture. This subjective 'taste' data will be used by the FA to suggest flavor, texture, color, aroma, or other attributes as may be recommended by the algorithm from the available filler components that may be added to the end product and as are compatible with the functional components to be used.

In one or more embodiments, supplements will typically be less than 1 gram of mass, whereas the ideal mass of the edible supplement pack is between about 30 and about 50 grams size when presented as a gel pack. So there is significant volume that can be added along with the active components to improve taste, texture, and other attributes that make the product more palatable. As compared to pills, tablets, capsules this is a comparative advantage in ingestibility by parts of the population.

The FA produces a data encoded recipe, which once approved by the individual consumer and any professional reviewer or licensed reviewer as may be required, is stored and logged for that individual order of an custom mixture. The stored formulation shall include data that constitutes the Bill of Materials ("BoM") required to assemble the custom mixture, including the list of all components to be included, their mass weights, solution strengths, and calculated volumes. This BoM also includes the sequence of assembly of the components to the custom mixture, using a production database of the components, and a process recipe that constrains the order of assembly such that the parameters and selection of the individual are produced.

A subsequently applied algorithm, the Process Algorithm ("PA") uses the BoM to create a machine sequence for automating the sequential or parallel assembly, process control, and quality assurance inline tests, and final homogenization of the custom mixture into an edible form. The custom mixture is assembled in accordance with the PA, via a highly automated and rapid process from a collection of ingredients that have been embedded at a known uniform concentration in semi-solid edible materials The assembled ingredients are then homogenized and/or solubilized and reformed into a desired stable semi-solid form such as a gel, suspension, or emulsion. Individual single servings are then packaged in easy to use disposable packets with labeling for that individual including person's name and date to consume.

In one or more embodiments, at the customer interface, the customer would be prompted with a series of questions concerning their age, sex, weight, family history of disease, resting pulse, current medications, any current diagnosis disease states, physiological parameters such as blood pressure, recent Ha1C levels, fasting glucose levels, glucose levels determined from blood glucose meter, cholesterol, HDL, LDL, serum liver enzymes. See, for example, FIG. 11.

In one or more embodiments, the interface would include an interface to input relevant genetic, metabolomics, proteomic, nutrigenonomic, allergy tests and other diagnostic data acquired from individual tests or from whole genome sequencing from providers like 23Andme®. Another option for the customer will be the option to import total personal datasets into the database from any existing database. Information would be stored in a query able data format such as MySQL. See, for example, FIG. 11.

In one embodiment of the customer interface, the customer will be given the option to input taste and texture preferences as compared to other known foods. For instance, a preference of sweet, sour, tart, spicy, and salty and texture preferences such as chewy, crunchy gummy etc.

In one embodiment, the FA will query independent sources such as the National Standards® database, Beer's List®, and National Institute of Health's Office of Dietary Supplements® for potential supplements that may have some benefit for the person's current health status based on input data and provide a list of those ingredients that have been shown by peer reviewed journals to have some level of health benefit. No claims of cures for efficacy or will be included in this output though references to third party public resources may be provided See, for example, FIG. 12.

In this embodiment the FA will calculate a dose for the desired ingredients by querying a database for appropriate dose based on body mass, age, sex, and any other known physiological conditions. See, for example, FIG. 12.

In one or more embodiments, the FA will identify contraindicating ingredients from independent sources such as National Standards® database, Beer's List®, and National Institute of Health's Office of Dietary Supplements® and notifies the customer of the risks. The computer interface may then offer the customer an option to confer with a professional nutritionist or health care provider. See, for example, FIG. 12.

In one or more embodiments, the FA may recommend a flavor and texture components for the individual based on the data from the customer input information.

In one embodiment, a storage media may be provided. The media may include ingredients such as dietary supplements (vitamins, minerals, proteins, amino acids, herbs, micro-dose allergens, and herbal extracts) are embedded at a uniform concentration into three dimensional semi-solid polymeric network. Such semi-solid structures are comprised of polymeric glycosaminoglycans, and polysaccharides like agar, carrageenan, alginate, natural gums, carboxymethyl cellulose, pectin, dextran, dextran derivatives, pullulan, xanthan, xyloglucan, starch, hyaluronic acid, or some combination thereof that exhibit thixotropic properties. Concentration and composition of polymeric components of the semi-solid structures may vary between about 0.1% and about 5% (w/w) depending on the final density and pH needed for ingredient addition, storage, and manipulation of semi-solid components.

In another embodiment of a storage media, ingredients such as therapeutic agents (drugs, oral vaccines, and biologics) are embedded at a uniform concentration into three dimensional semi-solid polymeric network hydrogels. Such semi-solid structures are comprised of polymeric glycosaminoglycans and polysaccharides like agar, carrageenan, alginate, natural gums, carboxymethyl cellulose, pectin, dextran, dextran derivatives, pullulan, xanthan, xyloglucan, starch, hyaluronic acid or some mixture of the preceding. Concentration and composition of polymeric components of the semi-solid structures will vary between about 0.1% and about 5% (w/w) depending on the final density and pH needed for ingredient addition, storage and manipulation of semi-solid components.

Figure 2:
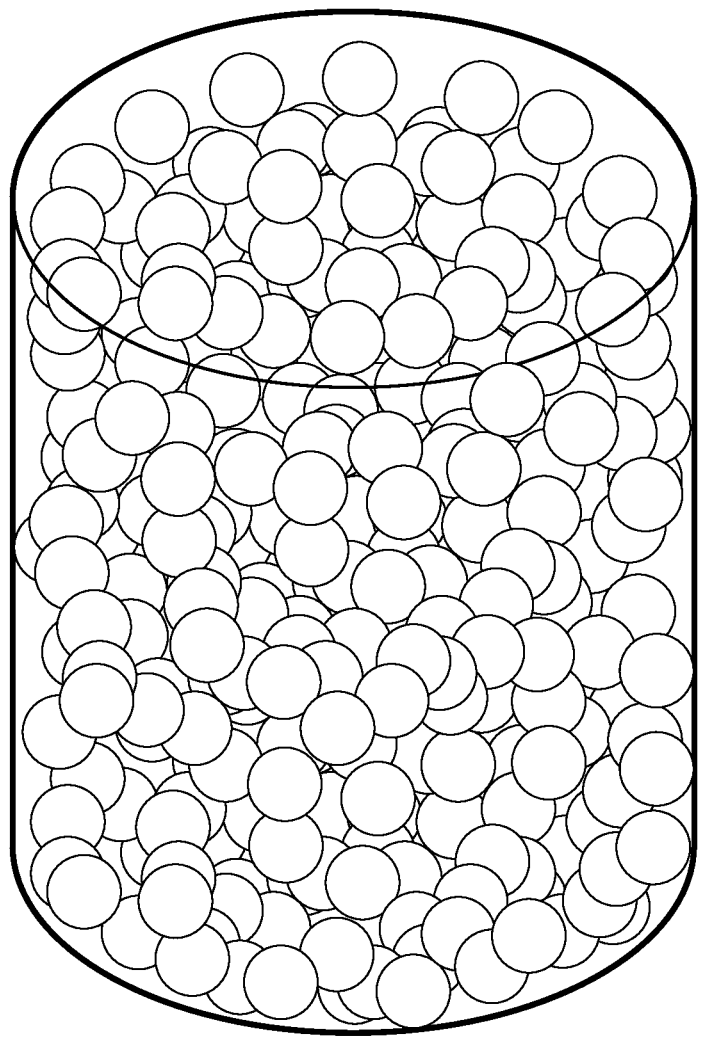
FIG. 2 illustrates uniform spheres of a supplement embedded into a semi-solid polymer matrix at a known number of spheres per unit of measure according to one or more embodiments disclosed herein.

Another embodiment of storage media, is to form uniform spheres of dietary supplements (vitamins, minerals, proteins, amino acids, herbs, and herbal extracts), fruit and vegetable extracts using the process of spherification, reverse spherification, or other known encapsulation process or microencapsulation methods such as three phase system. The process of spherification has been used been shown to work with other compositions such as propylene glycol alginate. For example the combination of several hydrocolloids has been shown to provide a means to vary key properties such as gelation and physical or chemical properties of the resultant hydrocolloid matrix see for example. Composite alginate hydrogels been shown to be useful for the controlled release of hydrophobic drugs, and allows solubilization of hydrophobic drugs. The food trend known as "molecular gastronomy" uses spherification and reverse spherification technique to create unique flavors and concentrate food flavors. In this invention the quantity of the ingredients in each sphere will be determined using a variety of measurement techniques as needed for that ingredient. The uniform spheres will then be embedded into the semisolid polymer matrix at a known number of spheres per unit of measure for example as shown in FIG. 2. The mass production of such microspheres of size ranging from a few microns to several millimeter using alginates and processes such as thermal shock of agars produces a means of to capture compounds that are not soluble in water or other edible liquid, and to produce these spheres in volume using parallel automation process.

Another embodiment of the storage media is to embed dietary supplements and therapeutics agents in semi-solid structures containing protein that has been cross-linked using transglutaminase. This technique to bond proteins together has been used extensively in the commercial food processing industry to create products such products as imitation crabmeat and fish balls.

The concentration of the ingredients in the semi-solid media will vary from between about 1×/mm and about 1000×/ml. For example, if the final dose is 10 mg and the ingredient is embedded at 10 mg/ml, then the equivalent of 1 ml will be added to the mixture. If the final dose is 10 mg and the embedded concentration is 1000 mg/ml, then the equivalent of 0.01 ml will be added to mixture.

Final mixture of the components can be achieved by dispersion via a dispersion mill, whisking, homogenization, resolublization using heat, adjusting pH, addition of cations, or any combination of these methods or any other known or known methods for mixing. During the final mixture various components necessary to improve flavor, texture, and stability will be adjusted accordingly. Such components include but are not limited to natural and synthetic flavors, emulsifiers such as lecithin, and stabilizers such as proteins, starch, pectin, plant particles, and of food gums. Final volumes for individual single serving size could range from hundreds of milligrams to 100 grams.

Machine and Automation Description

The purpose of the machine and automation design as described herein is to realize the custom mix recipe that is generated by the Formulation Algorithm into a physical assembly of all the compounds at the correct dose masses and volumes, and to do so with minimal manual intervention so as to be economic relative to convention means of nutritional or pharmaceutical such as pills, powders, and liquids. There are many potential automation system designs that may be able to produce such custom mixtures economically. Conventional approaches have been described using a multitude of precision liquid dispensers but such method have several technical faults, most notably that they co-mingle in solution the compounds to be delivered, such that they may interact with one another prior to ingestion. Such liquid dispensing methods also suffer from the ability to accurately dispense a known solution strength of many compounds, as over time, even a matter of minutes to hours, poorly soluble compounds go through natural gravity induced sedimentation, such that the active components either become dense to dilute from bottom to top of the liquid container, or tend to plate out the compound on the interior of the containment surfaces due to van der Waal or charge attraction of the materials and compounds. Such separation of the compounds from the liquid solution media causes production variation in the solution strength that is dispense, such that the volume dispensed contains widely varying molecular mass of the active compound. Such issues can be overcome by the addition of continuous kinetic or thermal energy to the solution, but such design are highly complex, use excessive energy when to maintain uniform solution strength in a known, state and inherently induce evaporation and thereby change in solution strength of the mixture. This may be notably true of natural, herbal, and lipid solution or oil bound compounds that cannot readily be held in a liquid suspension that is homogeneous at known solution strength per unit volume. Further liquid based solutions are prone to leaks, seepage, and other liabilities that may promote microbial contamination, and hence would pose ongoing sanitation requirements and would be more subject to production of unsafe mixtures.

Similar issues constrain powder based automation solutions, and these have other problems that also contribute to the non-uniform distribution of the active compound over the volume to be consumed to assemble the custom mixture. To overcome these issues, demands a complex and inefficient mechanism and one that that is highly instrumented to maintain predictable compound strengths as they are processed into the custom mixture.

Any of the above approaches, as well as others that have been considered by the inventors and are known to practitioners of such oral delivery systems, have been rejected not only due to their technical flaws, but because of the difficulty that would be inherent in scaling these designs into a system that is economic, secure, sanitary, accurate, and reliable in terms of availability and long times between failure. The embodiments of the automation system described herein address these disadvantages and shortcomings.

Figure 3:
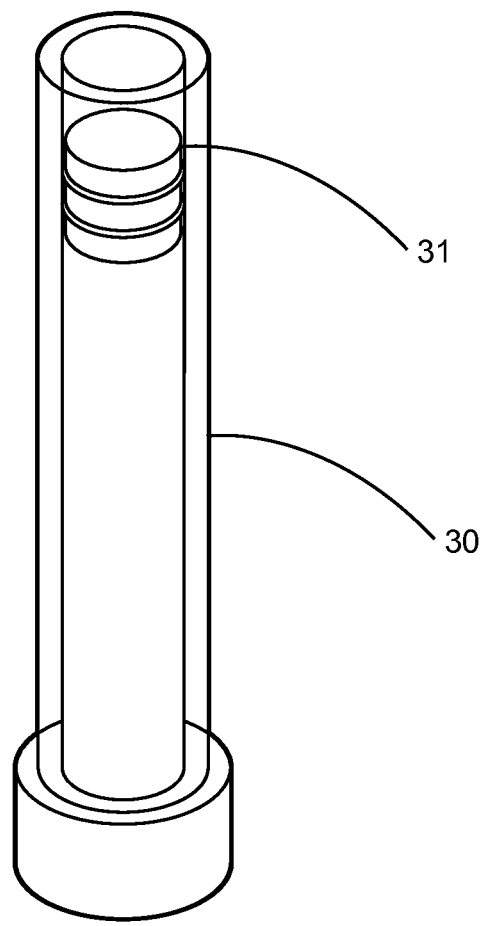
FIG. 3 illustrates a manner to contain hydrogel suspensions of compounds in a cylindrical tube constructed of low cost material according to one or more embodiments disclosed herein.

Embodiment 1 is illustrated in FIGS. 3 through 9 and is premised on the production of a container that has been prefilled with a known solution strength of each compound or combination of compounds. FIG. 3 illustrates a manner to contain the hydrogel suspensions of compounds in a cylindrical tube 30 constructed of low cost material such as polycarbonate, polystyrene, glass or other FDA approved materials, such that once all the compound is consumed in making custom formulations, this container is economic to dispose of when compared to the cost of a reusable container that must be cleaned and refilled. Container 30 includes a seal 31 that is actuated by linear motion of the one or more apparatuses disclosed herein to extrude a precise volume of compound evenly dispersed in the hydrogel media. The process of filling the container as illustrated in FIG. 3 may use conventional mixing techniques. For example, the hydrogel media, when in a liquid state, and prior to full cross linking would be dosed with the compound or compounds of interest and agitated to ensure uniform distribution of the compound into the suspension. Then the still liquid suspension mixture can be cast or poured into multiple container tubes at once, so producing a large number of filled containers in parallel. The filled tube containers may be cooled to the full cross linking temperature of the media or otherwise reacted so as to complete the transition to a semi-solid form, such as a gel. The gel strength that is required for this tubular container, such that it can be accurately dispensed as a semi-solid is a critical variable that will be controlled by the temperature, pH, viscosity as determined by a viscometer or increased resistance to stirring as measured by electrical resistance, and hydrogel percentage solution formulation, in accordance with the properties of the hydrogel media that is used. A similar process may also be used to produce multiple tubes in a concurrent batch using batch mixing techniques, containing the hydrogel with suspended micro encapsulated containers as illustrated in FIGS. 1 and 2.

In one or more embodiments, the mixture can be centrifuged if compounds are insoluble to increase solution density at the bottom of tubes. In this manner, you could pack insoluble compounds at high concentrations.

Each tube container may be identified and labeled with the name of the compounds suspended, the solution strength, the date and time of manufacture, a serial number identifier, and an estimated shelf life date, along with environmental storage requirements including temperature range, humidity, light exposure, etc that may affect the physical or chemical properties of the compound, the media, or the container. Solution strength in milligrams per milliliter for example for each compound carrier, along with validation of spectral signature match with the intended compound, by a method such as spectrographic measurement (RAMAN or mass spec) will be used to produce batch specific label information. Such labels will be printed and applied at time of batch production, such that they may be transport or stored prior to use. Such labels may contain an optical, RFID, or other manner of extracting the identity of the tube using an automated reader device and will be used by the automation system to ensure exact component identification and prevent improper incorporation of an ingredient into the mixture. In one or more embodiments, each tube or batch may have a verified solution concentration using analytical methods such as HPLC, MS/GC, raman, light spectrometry, visual inspection, or other.

Figure 4:
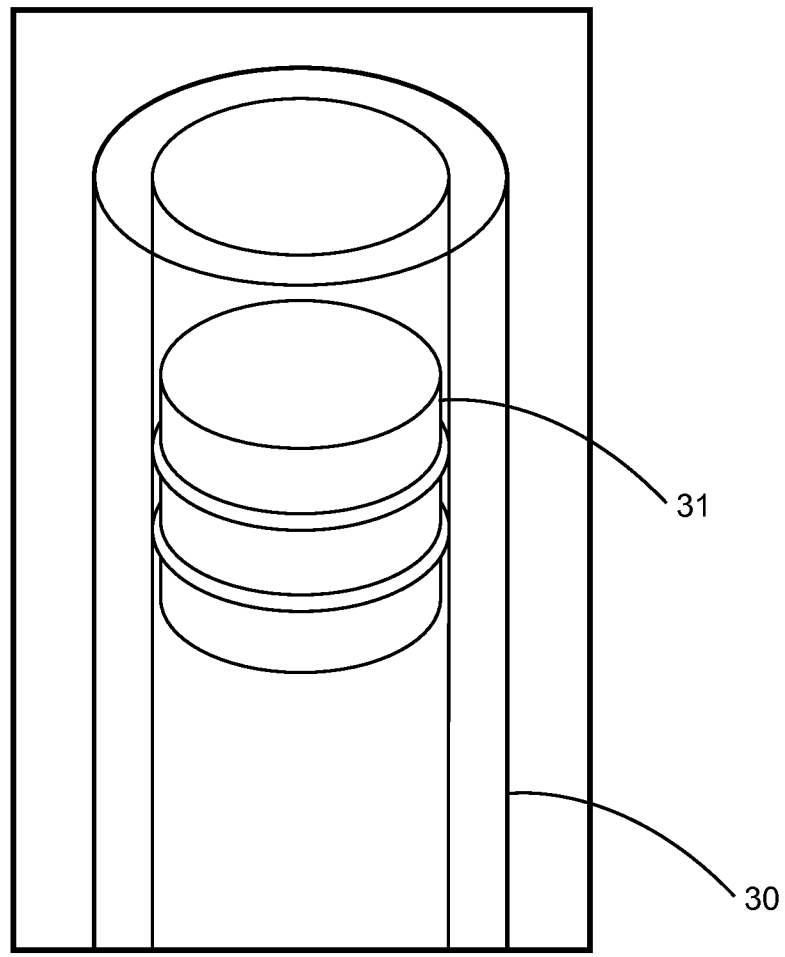
FIG. 4 illustrates a movable seal at the top end of the tube of FIG. 3 according to one or more embodiments disclosed herein.

As shown in FIG. 4, the one or more embodiments contain a movable seal at the top end of the tube. It would be closed at the bottom end with a removable seal, cap, or filter, which will be removed prior to use. The movable seal at the top also acts as a plunger that can be actuated in a linear manner to cause a precise amount of the hydrogel suspension to be pushed or extruded from the bottom of the sealed tube when open. A retention diameter, slightly smaller than the inner diameter of the tube container, at least 0.6% smaller approximately, may be provided by a ring such as a rubber "O" ring, which provides enough friction to prevent an uncontrolled extrusion of the media when the tube held in a vertical state is opened at the bottom end. This arrangement ensures that only once the top seal is actuate in a downward vertical manner will any amount of the media be extruded through the marginally smaller opening, thereby making this process under the full control of the linear actuation mechanism.

Table I shows examples of various tube diameters cross tabulated with potential solution strengths of compounds when 1 mm (0.039") of the media is extruded an relates it to the molecular mass that is contained in this volume. The simple relationship of diameter and length then controls the volume, such volume extruded is controlled by length of linear actuation times $\pi$ times the most constrained radius squared.

TABLE I

Actuator Linear Travel per dose example:
1 mm
0.039 inch

| Diameter (in) | Diameter (mm) | mg 0.01 x | mg .1 x | mg 1 x | mg 10 x | mg 100 x | mg 1000 x |
|---|---|---|---|---|---|---|---|
| 0.197 | 5 | 0.0079 | 0.7854 | 0.7854 | 7.8540 | 78.5398 | 785.3982 |
| 0.394 | 10 | 0.0157 | 1.5708 | 1.5708 | 15.7080 | 157.0796 | 1570.7963 |
| 0.591 | 15 | 0.0236 | 2.3562 | 2.3562 | 23.5619 | 235.6194 | 2356.1945 |
| 0.787 | 20 | 0.0314 | 3.1416 | 3.1416 | 31.4159 | 314.1593 | 3141.5927 |
| 0.984 | 25 | 0.0393 | 3.9270 | 3.9270 | 39.2699 | 392.6991 | 3926.9908 |
| 0.625 | 15.87525 | 0.0249 | 2.4936 | 2.4936 | 24.9364 | 249.3639 | 2493.6392 |
| 0.75 | 19.0515 19.05 | 0.0299 | 2.9924 | 2.9924 | 29.9237 | 299.2367 | 2992.3670 |

As is indicated in Table I, a lower or higher concentration of the molecular weight of the compound is extruded depending on the solution strength that is filled into the tubular container. So a one mm length of the media extruded from a 25 mm diameter container yields 0.039 milligrams of compound when filled with a 0.1 solution, compared to 39.3 mg if the tube is filled with a 10× solution strength. Given the very high density capacity of many of the studied hydrogels, it is possible for many highly water soluble compounds to achieve concentration as great at 1000×, thereby providing a large capacity of the active compound in a small cross-section of the tube container. At 10×, a 25 mm diameter tube that is 250 mm in length could provide up to 5000 doses of some compounds that are soluble at this strength. Conversely, a very dilute fill solution would require a much longer length of extrusion, but would inherently allow for microgram accuracy of solutions. This hydrogel filled container approach allows for dense physical storage for most compounds and provides for several variables that are means to optimize the storage versus accuracy of the process.

Figure 5:
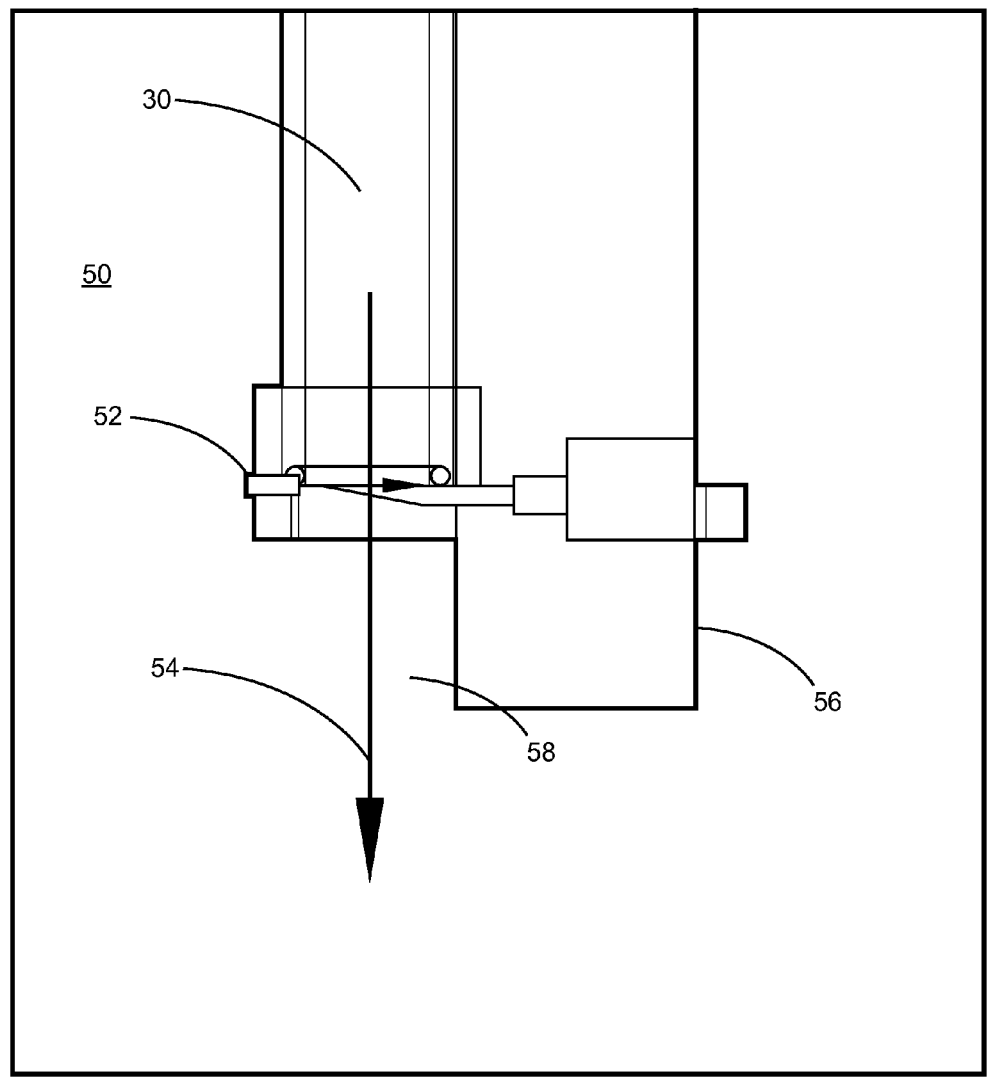
FIG. 5 illustrates a feeder apparatus according to one or more embodiments disclosed herein.
Figure 6:
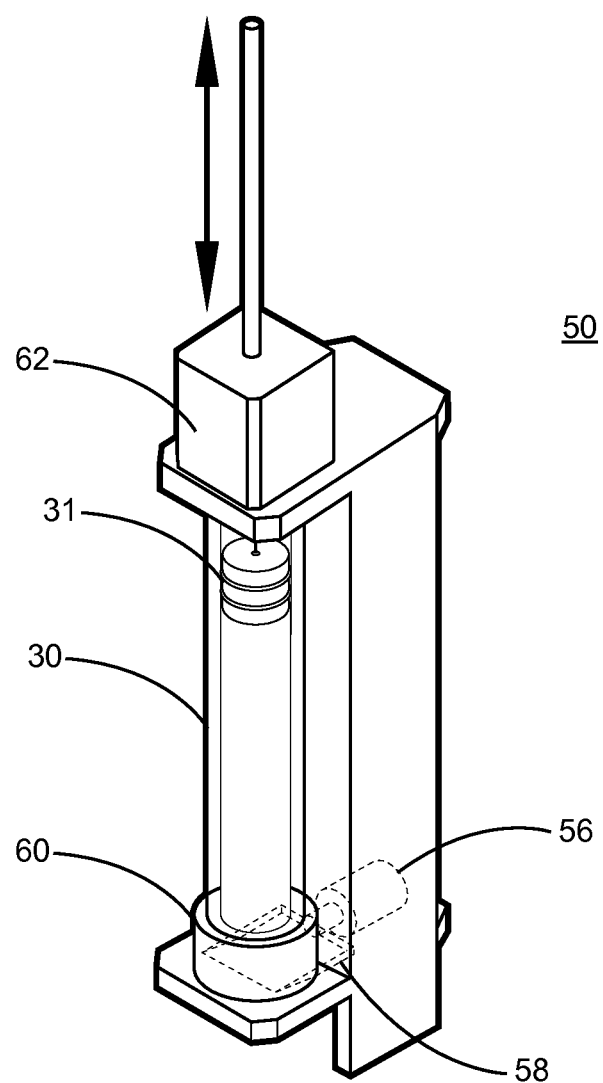
FIG. 6 illustrates a feeder apparatus according to one or more embodiments disclosed herein.

FIG. 5 illustrates a feeder apparatus 50 embodiment of a method whereby the dispensing of a compound is achieved, in which a precision cutting knife performs a double purpose of providing an air tight seal for the bottom of the container tube, and an edge 58 for cleaving away a precise length of the media once it has been extruded to a commanded length. The knife is controlled by a solenoid actuator 56. An optical photo sensor 52 or other non-contact sensor detects start of extrusion and arrow 54 indicates the path of component slice that is released. The feeder mechanism 50 as illustrated in FIG. 6 has a manner for securing the container tube of FIG. 3 via tube interlock 60, and a manner to attach the feeder mechanism to a linear actuator 62 at the top of the tube 30, such that the actuator 62 can drive the seal plunger assembly 31 of FIG. 4 in the vertical direction. The feeder assembly 50 of FIG. 6 incorporated a digitally controllable servo or stepper motor that can be commanded to produce a precise linear actuation in very repeatable displacements as commanded by the automation process control system. Each feeder may have a unique identification code or network address, as does each physical location that can accept a feeder on the machine. This network architecture enables the modularity of the machine design, allowing feeders conforming to the standard physical and electrical interface to be substituted for each other, in different locations, but to then identify to the process control algorithm their identity and the content of the compound type it holds. Rapid reconfiguration of the machines component inventory is an advantageous aspect of the system that allows it to accommodate an ever growing compliance to custom formulations, and new inputs. The feeder system, when commanded, will first open the bottom of the container tube by retracting the knife blade cover using a simple actuation such as an electrical solenoid. The process controller will then drive the linear actuator a predetermined distance that is proportional to the dose amount of the compound calculated by the Formulation final and approved recipe and as determined by the information conveyed by the label system of the tube container, such that the relationship of linear displacement distance as determined by the solution strength and the container diameter is accurately controlled to the molecular mass demanded in the recipe. An algorithm or table such as Table 1, embedded in the process automation control algorithm and whose parameters are set by the information conveyed by the container electronically read tube label produce the correct length of extruded compound. A non-contact manner, typically an optical photo switch, will detect the beginning of extrusion and its bottom edge, such that the length extruded begins once the detection of the bottom edge of the media is true, and then the linear actuator will continue to drive till the commanded length has been extruded. The next step is that the solenoid that opened the knife edge cover assembly is released, and with a rapid and straight parallel motion cleaves the length of extruded media from that in the container to produce a slice of component of the commanded length. This actuation of the knife cover would be performed by a passive mechanical, pneumatic, or magnetic force, such that no electrical or external power is needed to maintain closure of the tube bottom. The control of the feeder as embodied herein may be self-contained and removable or configurable to a machine base. The embodiment would include a local microprocessor controller, that can be networked with a standard network design, such as USB, CanBus, Ethernet, CAN Ether, RS-485, or other suitable multi-drop serial standard. The feeder connections to the machine to achieve control as described here may need only be this network connection and power to actuate the linear drive motor, solenoids, and sensors. This approach will highly facilitate rapid changeover of the machine configuration, allowing very fast setup of a new selection of compound feeders.

Figure 7:
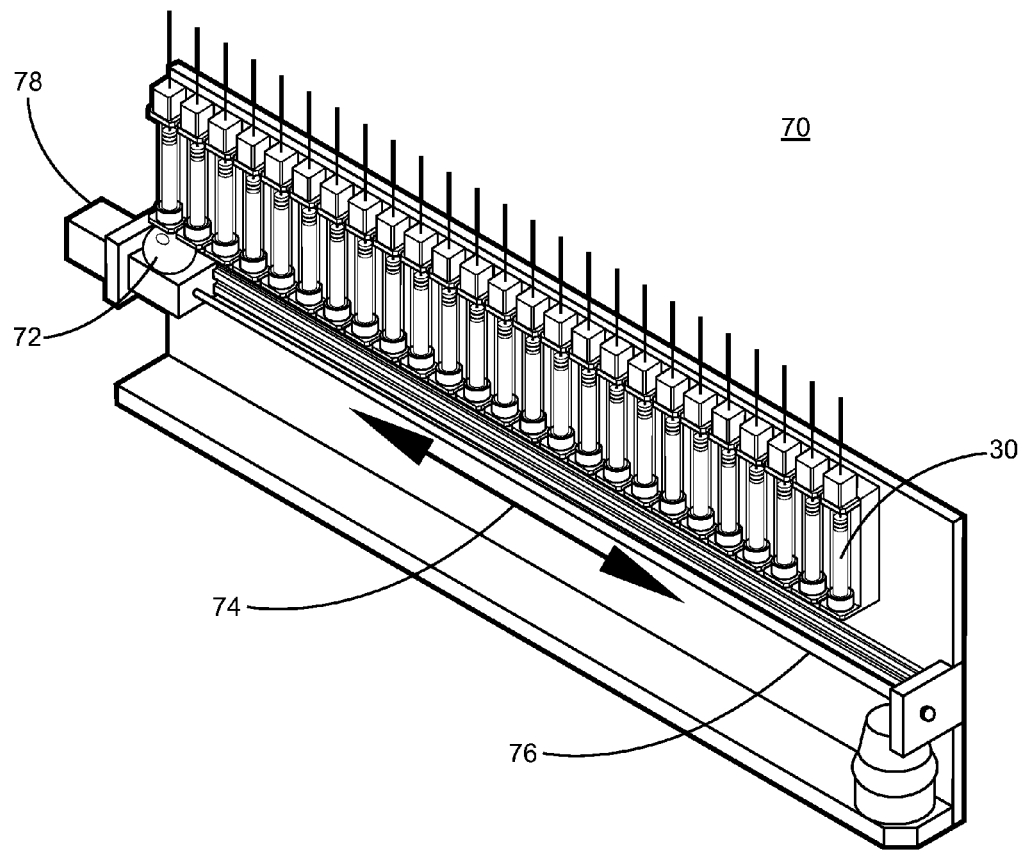
FIG. 7 illustrates a series of feeder apparatuses according to one or more embodiments disclosed herein.
Figure 8:
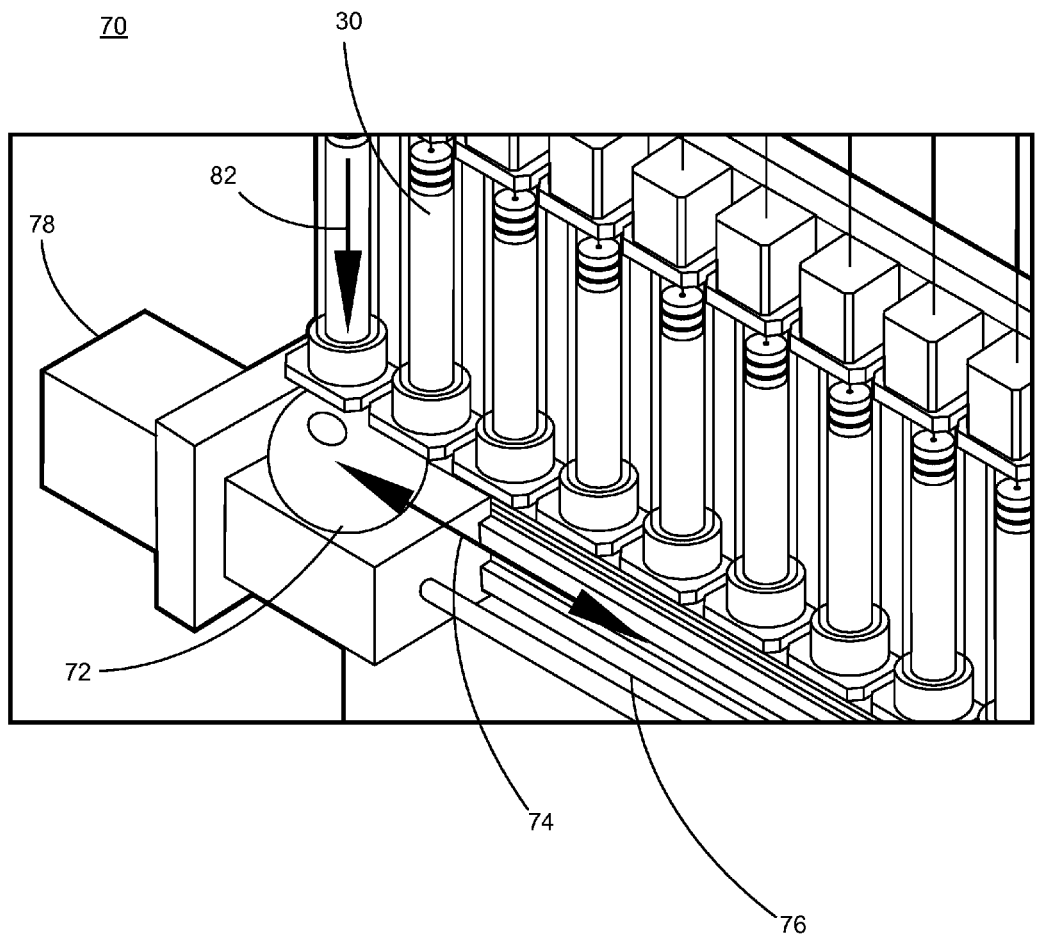
FIG. 8 illustrates an enlarged, partial view of the feeder apparatuses illustrated in FIG. 7 according to one or more embodiments disclosed herein.
Figure 15:
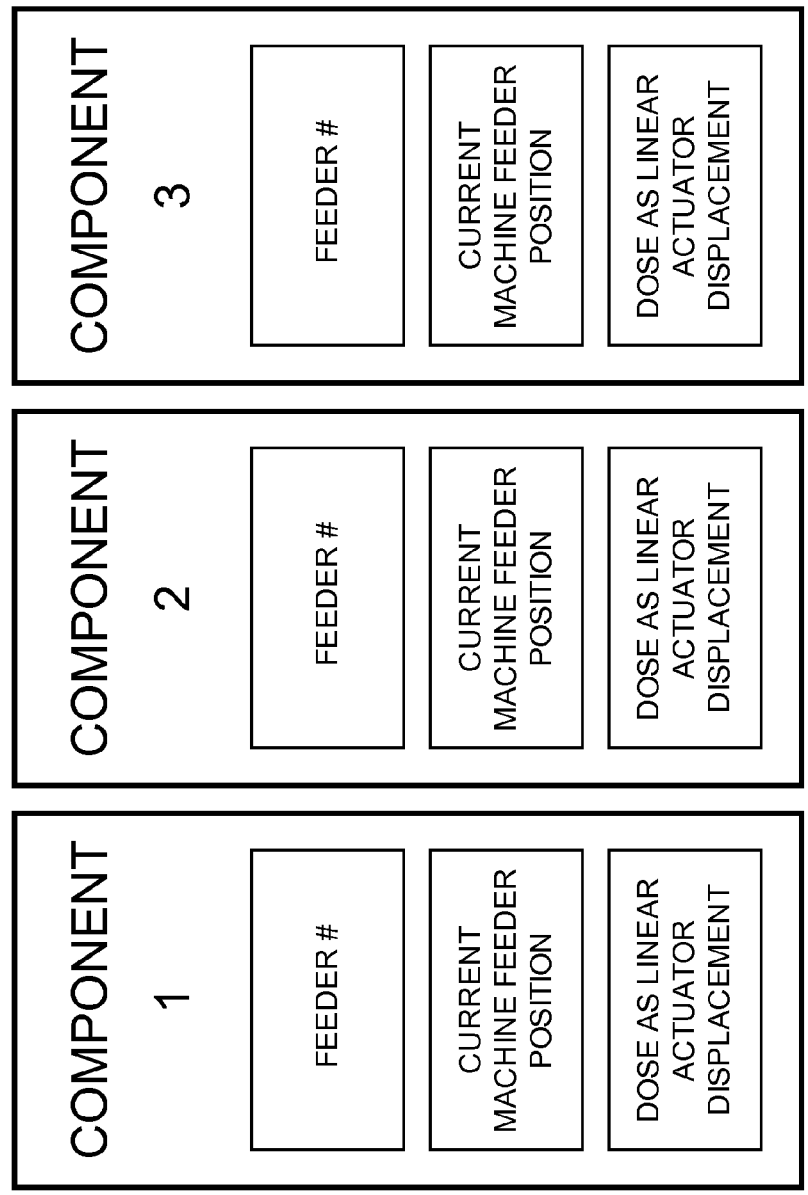
FIG. 15 illustrates a system diagram of a series of apparatuses according to one or more embodiments disclosed herein.
Figure 18:
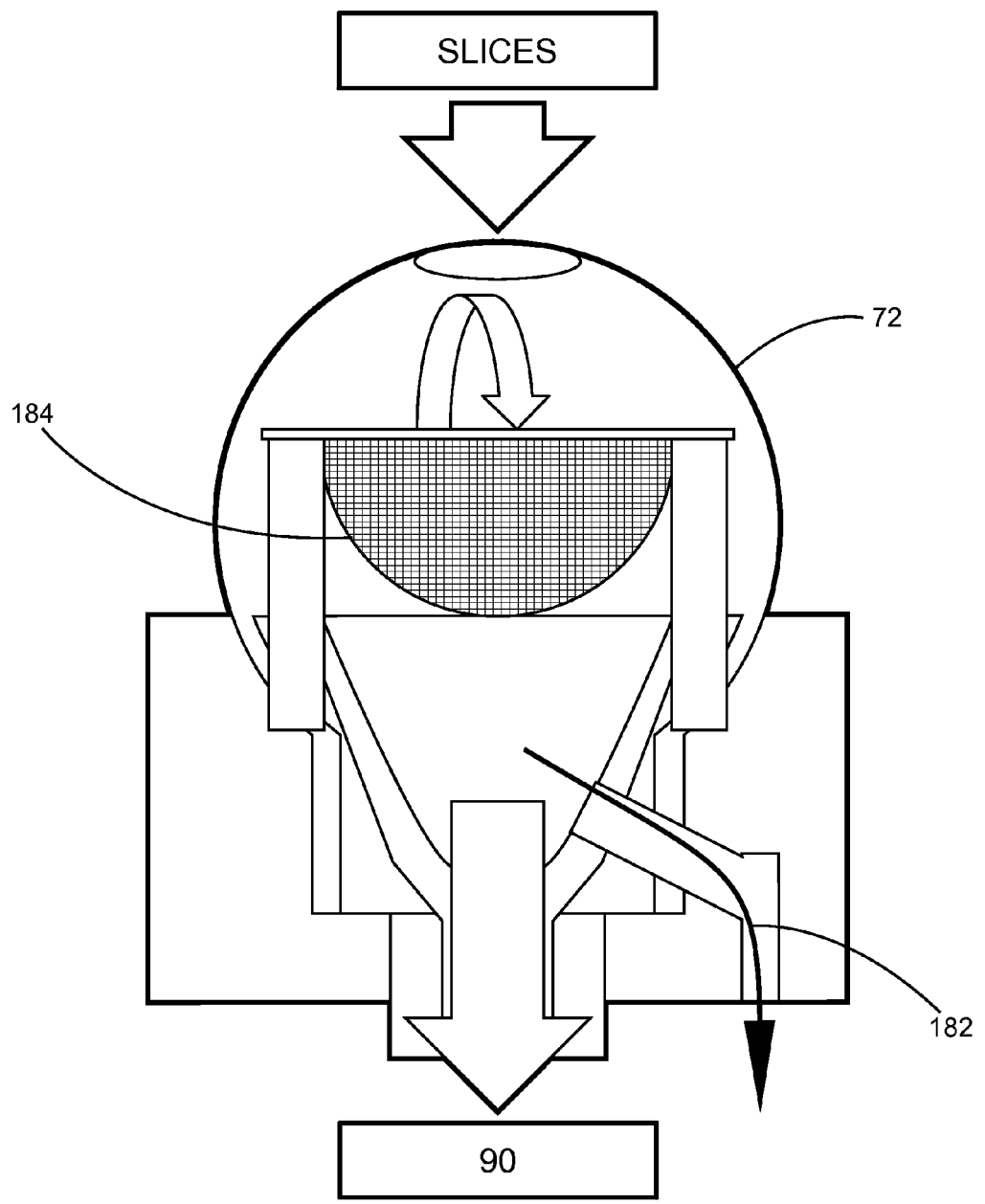
FIG. 18 is a front view of a collection vessel for collecting assembled compounds according to one or more embodiments disclosed herein.

The feeder apparatus as shown in FIG. 6 may be implemented as a very compact unit, such that many such feeders can be arranged in a small physical volume. As shown in FIG. 7, many feeders can fit in a short linear array, or little more than a meter, or might be arranged in an alternative configuration of a compact orbital fashion around a SCARA or other rotary actuator robot. FIG. 7 shows a linear configured robot 70 of a very simple design that integrates a number of feeders as described above onto a common frame. The main robotic linear axis 74 shown in FIG. 8 is driven by a similar servo of stepper controlled linear actuator 78 as is used by the compound feeders. The moving carriage on the robotic actuator carries a collection vessel 72 along guides 76 to catch and collate the output of each feeder as it completes the sequence described above, and as instructed by the process controller with an assembly sequence as diagrammed in FIG. 15. The collection vessel 72, for example such as FIG. 18, may include a stainless mesh basket 184 to catch cleaved component slices and may be augmented with vacuum suction 82 so to assure that the cleaved length of media cut from the feeder will be collected positively. This is an important innovation in that some of the solutions strengths might result in very thin slices being cleaved, where the material is dispensed according to directional arrow 82, such that they have light mass and may not fall directly down, but drift in the air laterally if not assisted. The vacuum pull of the collection vessel will begin operating just before the knife cover closes so at to obtain control of the output slice, until that slice has fallen into the interior of the collection vessel. The bottom of the collection vessel may contain a precision strain bridge to weight the resultant sliver, and that weight that is detected will be compared by the process control system to the expected weight of the added media. If this weight does not correspond, then the vessel will be able to eject the output and command a retry of the feeder. Once a successful mass of the compound is verified to be in the collection vessel, the robot actuator will be commanded to travel to the location of the next feeder from which a contribution of component is commanded. This process repeats until all the compounds have been collected that are specified in the custom mix recipe.

Figure 9:
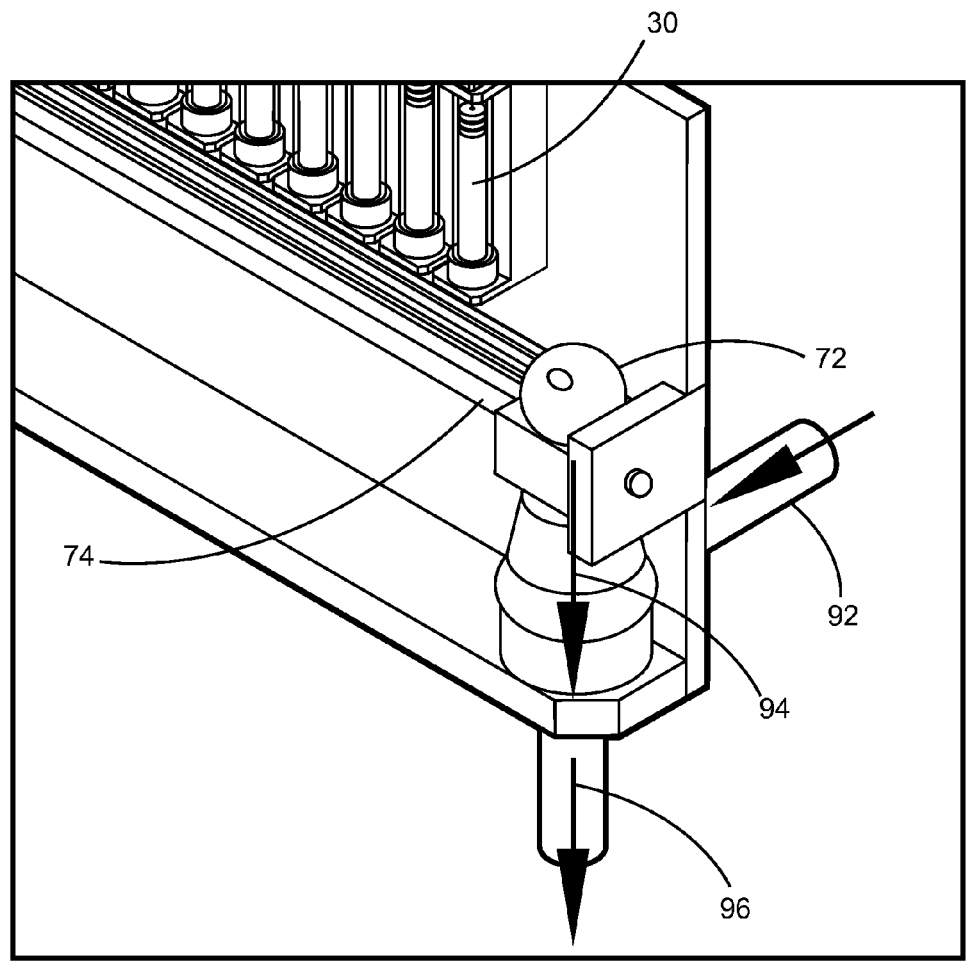
FIG. 9 illustrates transport of assembled compounds according to one or more embodiments disclosed herein.

Once the full collection of the component compounds is completed by accessing all of the demanded feeders, then the robotic actuator will take the collection vessel 72 to a station above a device for homogenization and blending of the assembled compounds 94, as shown in FIG. 9. A door for the homogenizer unit 90, effectively a blender, will automatically be opened by a commanded solenoid, and the entire contents of the containment vessel will be emptied under vacuum and air blast into the homogenizer chamber. Once the collection vessel is emptied, the homogenizer door closes and the process of blending and macerating the assembly commences. A valve will meter from another source, a volume of liquid, gel, or semi-solid into the homogenizer chamber containing other filler or nutritional materials 92 in a calculated volume to make the desired total volume for the individual serving package for a single day or the multiple serving packages to a total volume for multiple days. This input filler may be an organic liquid, for example fruit juices or extracts, gelled edible composites, semisolid, or just added water and may contain flavors, textures, and the like intended to make the resultant compound more palatable. A similar system may feed this input to accommodate the taste preferences captured in the profile. The homogenizer 90 blends, macerates, and turns all inputs into a consistent product via direction arrow 94, to the extent that this process produces a desirable product, under control of time, speed of blending, form of maceration tool, or cutting blades, as may be suited to the algorithms controlling the process automation and optimization based on the combined properties of the known inputs to the mixture, for example to make the output "chunky" or "smooth" or any variant of textures.

Figure 14:
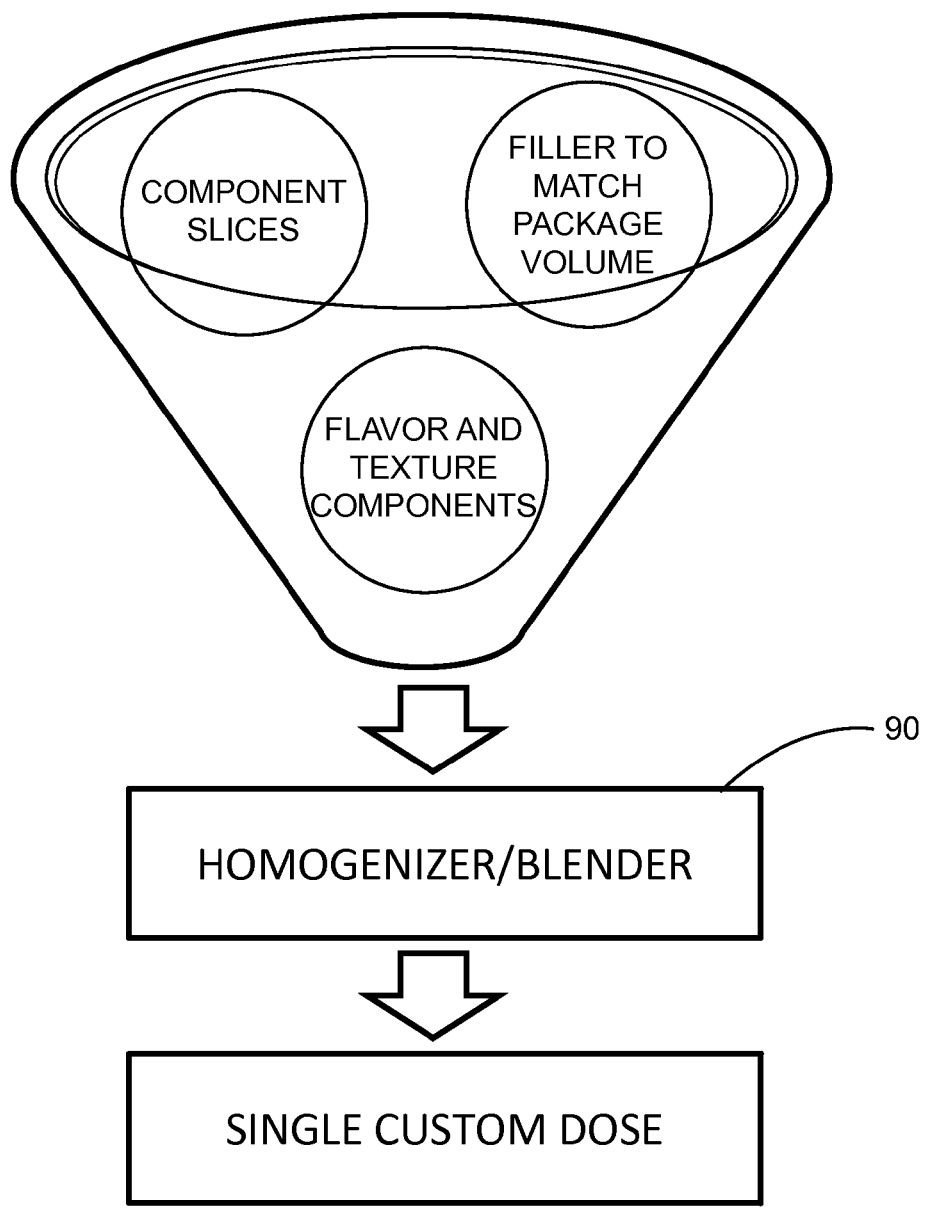
FIG. 14 illustrates a flow diagram of one or more methods according to one or more embodiments disclosed herein.

After homogenization and volume completion in this step, the effluent of the homogenizer is ejected through a valve and is now ready for packaging into the edible consumable format. FIG. 14 diagrams the components of the post assembly homogenization step that results in either a single or multiple volume edible product of the custom formulation. The homogenizer/blender 90 receives material formed from component slices, filler to fill out the package volume, and flavor and texture components. The homogenizer/blender then forms a single custom dose.

Multiple lines such as shown in FIG. 7 can be combined parallel, concurrent production to increase the number of online compounds or components. In one embodiment that uses the inherent modularity, the output of two or more such lines into a common homogenizer would provide a manner to have a larger number of components simultaneously online, with the impact of a dramatic reduction in machine configuration setup time. For example, a line with 24 components combined with another of 24 components would have an online inventory of 48 components that can be used in the formulation required, without any machine and feeder reconfiguration. This approach would also support multiple homogenizers, and with basic plumbing, the outputs and inputs of the lines can be combined to produce a larger and more rapidly created input for the packaging process.

In another embodiment, a similar feeder for the compounds is used in a way that these feeders are accessed concurrently and in parallel, such that all components needed to make the formulation are dispensed in the specified proportions into a carrier medium, such that the filler media that makes up much of the output of the edible product. This approach would have potential of a very high throughput when compared to the sequential assembly process using the robotic collector approach of the first discussed embodiment. This embodiment would have advantages in speed at the cost of greater complexity of plumbing the flows. While sharing a common implementation of the FA, the process algorithm would be significantly different as regards machine control. The homogenization process would be similar to the one in the first implementation, but would combine the parallel flows from the feeder with the filler in final step before packaging.

In another embodiment of the automation, the feeder mechanism as shown in FIG. 6 is replaced by a tape feed device similar to that used in high speed surface mount electronics assembly. The dietary supplement or therapeutic agent in this system would be enmeshed in a hydrocolloid matrix as per the description above, but with a formulation of the hydrocolloid such that is it suitable for post gel formation desiccation, removing some or all of the water content. The effect of desiccation of the compound bearing a hydrogel formulation would be to shrink its volume and also to make the component more physically rigid and stable to enable packaging and handling of it by automation, akin to "pick and place" SMD assembly machines. Such componentization of the compounds in SMD sized formats would allow for large online inventories of components. By varying the volume and the solution strength of the compound enmeshed with the hydrogel, a large range of quantized doses can be predefined, produced, and packaged in this way. The advantage of this approach would be to further reduce the space of storage of a large variety of pre-packaged components, but at the expense of further steps to dessicate, cut, and package the component, as compared to the tube feeder method shown in FIG. 6. This method may not be very applicable to compounds that need to be supplied dissolved in lipids and/or oils or that require viability of the materials in biological forms (biologics, live vaccines, stem cells, etc) and so require retention of water in the packaging. Also the cost of formulating, forming, and packaging the pre-defined doses on tape is considerably more expensive and demands a high knowledge of the user rates of consumption to justify the investment.

Another embodiment that has potential for high volume customization is to use the techniques as learned from the 3D printing technologies. Also known as 3D lithography, this technology is directed at the production of discrete artifacts and parts made of plastic, polymer, or sintered metal whose shape is determined by a Computer Aided Design data set to driving a printer style machine that builds up the specified design in vertical stratification. Some of these principles can be applied to the custom formulation of nutraceuticals or pharmaceuticals as an embodiment of the subject matter disclosed herein. A hydrogel or digestible polymers can be loaded with known solution strength of active compounds and then extruded as a mononfilament cable or string. This string can then be cut to length to arrive at a specified dose. In this embodiment, the monofilament dietary supplement or therapeutic agents filled string become a continuous cylinder like that of FIG. 6. This method of feeding components as monofilament polymer matrix with embedded active compounds has advantages in the formation of other non-oral feeding methods such a suppositories where 3D shape may be important, or implantable prosthetic devices with active drug release. This approach would enable miniaturization to make very small machine system feed by spools or cassettes or print cartridges containing the components with the same functionality of variable input of active compound level to a custom mix.

Packaging

In an embodiment the final mixture will be dispensed in a disposable packet, bottle, cup, or other container which will be labeled with person's name, date to use, flavor and other pertinent information indicating a customized formulation. This approach will aid compliance and give clear labeling of contents for end users.

According to one or more embodiments, a system is provided. The system includes a computing device configured to receive health-related information from one of an individual, their agent, or a service provider, receive taste-related preference data from a individual, based on the health-related information, determine a formulation for a supplement for the individual, and based on the taste-related preference data, determine a filler medium that is consistent with the taste-related preference data. The system further includes a formulation module configured to prepare the formulation, a medium formulation module configured to prepare the filler medium, and a dispenser configured to dispense a predetermined amount of the formulation within the filler medium to form a dosage.

According to one or more embodiments, health-related information includes one of medical history, height, weight, age, and sex of the individual. Health-related information may include family history, genetic, allergy profile, and metabolomic profile data of the individual.

According to one or more embodiments, taste-related preference data includes taste, texture, and size of dosage.

According to one or more embodiments, the filler material is semi-solid and/or edible.

According to one or more embodiments, the filler material is a hydrocolloid.

According to one or more embodiments, the filler material is a nutritional filler.

According to one or more embodiments, the formulation includes multiple components of compounds.

According to one or more embodiments, the dosage is configured as a daily dosage.

According to one or more embodiments, the dispenser is configured to dispense the formulation in uniformly distributed manner.

According to one or more embodiments, the system further includes a server in communication with the computing device that includes a data bank having individual parameters affecting dosing levels. The individual parameters include age, sex, body mass, circumstantial health status, laboratory tests of levels of compounds onboard, and current consumption level of compounds.

According to one or more embodiments, the system includes a server in communication with the computing device that includes a data bank having available compounds that have associated scores of relevancy, efficacy, and safety in relation to the health-related information from the individual.

According to one or more embodiments, the computing device is configured to determine appropriate dosing requirements based on the health-related information of the individual. The health-related information includes ones of age, sex, body mass, circumstantial health status, and current consumption level of compounds.

According to one or more embodiments, the dispenser uses at least one of controlled actuation, pressure, compression, and displacement to determine a desired mass or volume of the formulation within a dosage.

According to one or more embodiments, the computing device is configured to determine a molecular mass of formulation, and further wherein the dispenser is configured to dispense the determined molecular mass of formulation.

According to one or more embodiments, the formulation module may include one or more containers having a formulation therein, and the computing device may be configured to compare an electronic identification of each of the containers and a desired formulation.

According to one or more embodiments, the formulation module is configured to prepare the formulation from a plurality of compounds.

According to one or more embodiments, the computing device is configured to determine a pattern for a given individual in which multiple doses are ingested daily and based on the pattern, determine a formulation that includes the multiple doses. The dispenser is configured to dispense the formulation that includes the multiple doses into a single filler medium for a given day of dosages. In this manner, health-related data could be monitored as a person consumes the one or more compounds/supplements provided herein. As one example, if a person had low iron levels before ingesting the supplement, a first elevated iron level could be mixed with a compound. After a period of treatment, the person's health information could be monitored, and if iron levels were then at normal levels, a lower amount of iron could be mixed with the formulation.

While the embodiments have been described in connection with the preferred embodiments of the various figures, it is to be understood that other similar embodiments may be used or modifications and additions may be made to the described embodiment for performing the same function without deviating therefrom. Therefore, the disclosed embodiments should not be limited to any single embodiment, but rather should be construed in breadth and scope in accordance with the appended claims.

What is claimed:

1. A system comprising:
a computing device configured to:
receive health-related information for an individual from the individual, their agent, or a service provider, the health-related information including one of genetics or metabolomic profile data of the individual;
receive taste-related preference data from the individual;
based on the health-related information, determine a formulation for an ingredient for the individual; and
based on the taste-related preference data, determine a filler medium that is consistent with the taste-related preference data, wherein the filler medium is a thixotropic semi-solid hydrocolloid that allows dissolution or suspension of compounds in a form that is stable until agitated or extruded at which point the semi-solid hydrocolloid becomes fluid and can be dispensed;
a preparation apparatus comprising:
a formulation device configured to prepare the formulation;
a medium formulation device configured to prepare the filler medium; and
a dispenser configured to dispense a predetermined amount of the formulation within the filler medium to form a dosage,
wherein the thixotropic semi-solid hydrocolloid is solubilized to embed the formulation and then reformed as a semi-solid,
wherein the dosage is packaged as an individual use dosage in a packaging material.

2. The system of claim 1, wherein health-related information further includes one of medical history, height, weight, age, and sex of the individual.

3. The system of claim 1, wherein health-related information further includes one of family history, and allergy profile data of the individual.

4. The system of claim 1, wherein taste-related preference data includes taste, texture, and size of dosage.

5. The system of claim 1, wherein the ingredient is a supplement.

6. The system of claim 1, wherein the ingredient is a pharmaceutical product.

7. The system of claim 1, wherein the filler medium is edible.

8. The system of claim 7, wherein the filler medium is a nutritional filler.

9. The system of claim 1, wherein the formulation includes multiple components of compounds.

10. The system of claim 1, wherein the dosage is configured as a daily dosage.

11. The system of claim 1, wherein the dispenser is configured to dispense the formulation in a uniformly distributed manner.

12. The system of claim 1, wherein a server is in communication with the computing device, and the server includes a data bank having individual parameters affecting dosing levels,
wherein the individual parameters include age, sex, body mass, circumstantial health status, and current consumption level of compounds.

13. The system of claim 1, wherein a server is in communication with the computing device, and the server includes a data bank having available compounds that have associated scores of relevancy, efficacy, and safety in relation to the health-related information from the individual.

14. The system of claim 1, wherein the computing device is configured to:
determine dosing requirements based on the health-related information of the individual,
wherein the health-related information includes ones of age, sex, body mass, circumstantial health status, and current consumption level of compounds.

15. The system of claim 1, wherein the dispenser uses at least one of controlled actuation, pressure, compression, and displacement to determine a desired mass or volume of the formulation within a dosage.

16. The system of claim 1, wherein the computing device is configured to determine a molecular mass of formulation, and further wherein the dispenser is configured to dispense the determined molecular mass of formulation.

17. The system of claim 1, wherein the formulation device includes one or more containers having a formulation therein, and further wherein the computing device is configured to compare an electronic identification of each of the containers and a desired formulation.

18. The system of claim 1, wherein the formulation device is configured to prepare the formulation from a plurality of compounds.

19. The system of claim 1, wherein the computing device is configured to:
determine a pattern for a given individual in which multiple doses are ingested daily; and
based on the pattern, determine a formulation that includes the multiple doses,
and further wherein the dispenser is configured to dispense the formulation that includes the multiple doses into a single filler medium for a given day of dosages.

20. The system of claim 1, wherein the computing device is configured to:
receive individual alterations to each of the formulation and filler medium;
determine whether individual alterations to each of the formulation and filler medium are within acceptable contraindication ranges.

21. The system of claim 20, wherein the computing device is configured to store a profile on the individual.

22. The system of claim 21, wherein the profile includes at least one of medical history, family medical history, nutritional, dietary, and pharmacological product consumption.

23. The system of claim 20, wherein the computing device is configured to determine a formulation relevancy score based on the health-related information and suggested formulation.

24. The system of claim 23, wherein the computing device is configured to display the formulation relevancy score to the individual.

25. The system of claim 20, wherein the computing device is configured to determine a filler relevancy score based on the taste-related preference data and suggested filler.

26. The system of claim 25, wherein the computing device is configured to display the filler relevancy score to the individual.

27. The system of claim 20, wherein, when the computing device determines that individual alterations to each of the formulation and filler medium are not within acceptable contraindication ranges, the computing device communicating a request for independent review by a health care professional.

28. The system of claim 20, wherein the computing device is configured to display, on a user interface, a series of health-related questions for response by the individual forming the health-related information.

29. The system of claim 20, wherein the computing device is configured to display, on a user interface, a series of taste related-preference data for response by the individual forming the taste-related preference data.

30. The system of claim 1, wherein the health-related information includes genetics profile data of the individual.

31. A product made according to a process,
wherein the product comprises:
a filler medium that is a thixotropic semi-solid hydrocolloid that allows dissolution or suspension of compounds in a form that is stable until agitated or extruded at which point the semi-solid hydrocolloid becomes fluid and can be dispensed;
a formulation for an ingredient for an individual and contained within the filler medium, the ingredient based on health-related information;
wherein the product is made according to the process comprising:
receiving the health-related information for the individual from the individual, their agent, or a service provider, the health-related information including one of genetics or metabolomics profile data of the individual;
receiving taste-related preference data from the individual;
based on the health-related information, determining a formulation for an ingredient for the individual;
based on the taste-related preference data, determining the filler medium that is consistent with the taste-related preference data;
preparing the formulation;
preparing the filler medium;
dispensing a predetermine amount of the formulation within the filler medium to form a dosage, wherein the thixotropic semi-solid hydrocolloid is solubilized to embed the formulation and then reformed as semi-solid.

* * * * *